US008357096B2

(12) United States Patent
Jeong et al.

(10) Patent No.: US 8,357,096 B2
(45) Date of Patent: Jan. 22, 2013

(54) NOISE REDUCTION AND ALIASING COMPENSATION IN A DOPPLER MODE IMAGE

(75) Inventors: Mok Kun Jeong, Seoul (KR); Sung Jae Kwon, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 972 days.

(21) Appl. No.: 12/351,740

(22) Filed: Jan. 9, 2009

(65) Prior Publication Data

US 2009/0182236 A1 Jul. 16, 2009

(30) Foreign Application Priority Data

Jan. 10, 2008 (KR) .................... 10-2008-0002851

(51) Int. Cl.
*A61B 8/00* (2006.01)
(52) U.S. Cl. ........ 600/453; 600/407; 600/437; 600/455; 600/457; 600/458
(58) Field of Classification Search .................. 600/407, 600/437, 453–454; 382/128
See application file for complete search history.

(56) References Cited

U.S. PATENT DOCUMENTS

| | | | |
|---|---|---|---|
| 4,542,657 A * | 9/1985 | Barber et al. ............... | 73/861.25 |
| 4,932,415 A | 6/1990 | Angelsen et al. | |
| 5,487,389 A * | 1/1996 | Banjanin et al. ............. | 600/455 |
| 5,544,658 A | 8/1996 | Kim et al. | |
| 6,447,455 B2 | 9/2002 | Bang et al. | |
| 6,480,142 B1 * | 11/2002 | Rubin ........................ | 342/26 R |
| 6,859,659 B1 | 2/2005 | Jensen | |
| 2003/0158484 A1 | 8/2003 | Pan et al. | |
| 2005/0054931 A1 | 3/2005 | Clark | |
| 2007/0016073 A1 | 1/2007 | Kim et al. | |
| 2008/0242994 A1 * | 10/2008 | Tamura ........................ | 600/453 |

FOREIGN PATENT DOCUMENTS

| | | |
|---|---|---|
| KR | 100381874 B1 | 4/2003 |
| KR | 1020060124824 A | 12/2006 |
| WO | WO 2007/023438 A2 | 3/2007 |

OTHER PUBLICATIONS

Kasai et al., "Real-Time Two-Dimensional Blood Flow Imaging Using an Autocorrelation Technique," IEEE Transactions on Sonics and Ultrasonics, vol. SU-32, No. 3, pp. 458-464, May 1985.
European Search Report for EP 09000128.0-1526/2078494, 6 pages, mailed Nov. 20, 2009.

* cited by examiner

*Primary Examiner* — Tse Chen
*Assistant Examiner* — Joel F Brutus
(74) *Attorney, Agent, or Firm* — McDermott Will & Emery LLP (57) ABSTRACT

The present invention relates to an ultrasound system and a method of forming a Doppler mode image. The ultrasound system comprises a transmission/reception unit operable to transmit/receive ultrasound signals at a pulse repetition frequency (PRF) to form an n number of Doppler signals. The ultrasound system further comprises a signal processing unit. The signal processing unit computes a first mean frequency based on an $n^{th}$ Doppler signal and an $(n-1)^{th}$ Doppler signal and a second mean frequency based on an $n^{th}$ Doppler signal and an $(n-k)^{th}$ Doppler signal, wherein k is a positive integer equal to or greater than 2. The signal processing unit estimates a Doppler frequency and compensate for aliasing of the Doppler signal based on the first and second mean frequencies to produce Doppler signal with the aliasing compensated. An image processing unit operable to form a Doppler mode image based on the Doppler signals produced by the signal processing unit.

18 Claims, 5 Drawing Sheets

NOISE REDUCTION AND ALIASING COMPENSATION IN A DOPPLER MODE IMAGE

The present application claims priority from Korean Patent Application No. 10-2008-0002851 filed on Jan. 10, 2008, the entire subject matter of which is incorporated herein by reference.

BACKGROUND OF THE INVENTION

1. Technical Field

The present invention generally relates to ultrasound systems, and more particularly to an ultrasound system and a method for reducing noise and compensating aliasing in a Doppler mode image.

2. Background Art

An ultrasound system has become an important and popular diagnostic tool since it has a wide range of applications. Specifically, due to its non-invasive and non-destructive nature, the ultrasound has been extensively used in the medical fields. Modern high-performance ultrasound diagnostic systems and techniques are commonly used to produce two or three-dimensional diagnostic images of internal features of an object (e.g., human organs).

Generally, the ultrasound system may provide a brightness (B) mode for displaying a 2-dimensional image based on reflection coefficients of ultrasound signals in a target object, a Doppler mode for displaying an image of a moving object (e.g., blood flow) by using a Doppler effect, and an elasticity mode for displaying an image of a target object based on displacements of the target object before and after applying compression. In the Doppler mode, a Doppler mode image may be formed by using a frequency change (hereinafter, referred to as "Doppler frequency") between a frequency of an ultrasound signal transmitted from a probe hereinafter, referred to as "transmit frequency") at a pulse repetition frequency (PRF) and a frequency of a Doppler signal reflected from a moving object (hereinafter, referred to as "receive frequency"). The Doppler mode image may be formed based on the characteristics in which the receive frequency for the target object moving toward the probe is higher than the transmit frequency and the receive frequency for the target object moving away from the probe is lower than the transmit frequency.

When the Doppler frequency is higher than ±PRF/2 in the Doppler mode, aliasing may occur. Thus, a high Doppler frequency may be misinterpreted as a low Doppler frequency and vice versa. As such, a direction of the blood flow may be incorrectly identified. Various methods for compensating for the aliasing have been introduced in the art. However, the conventional methods may compensate for the aliasing without considering noise in the Doppler signal. Accordingly, since the Doppler frequency may fluctuate between ±PRF/2 in approaching PRF/2 due to noise, detection and compensation of the aliasing may not be correctly carried out.

DETAILED DESCRIPTION OF THE INVENTION

Figure 1:
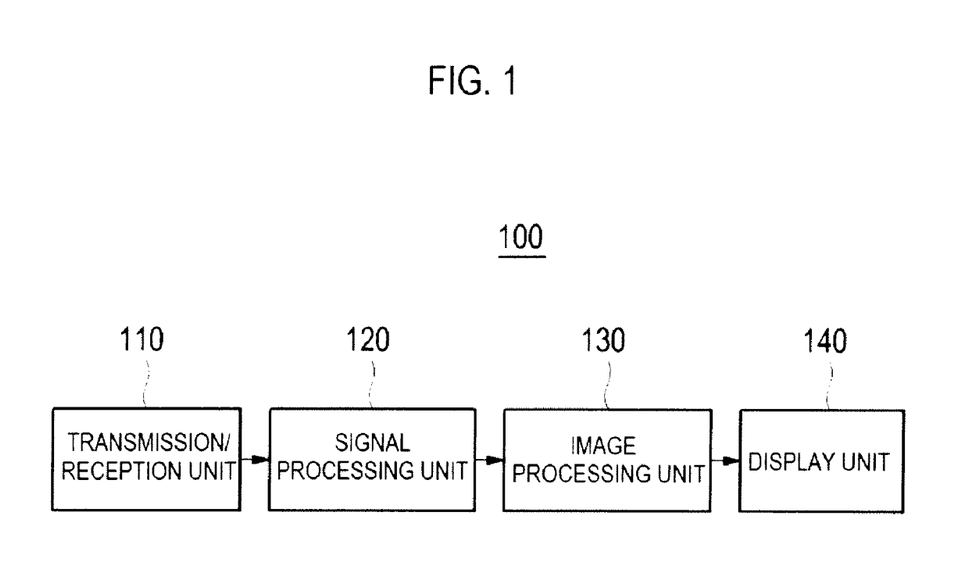
FIG. 1 is a block diagram showing one embodiment of an ultrasound system.

FIG. 1 is a block diagram showing one embodiment of an ultrasound system. As shown in FIG. 1, the ultrasound system 100 may include a transmission/reception unit 110 that may transmit an ultrasound signal to a region of interest at a pulse repetition frequency (PRF) and receive an ultrasound echo to thereby form a Doppler signal. The transmission/reception unit 110 may include a probe (not shown) for transmitting and receiving the ultrasound signal and a beamformer (not shown) for performing transmit focusing and receive focusing.

The ultrasound system 100 may further include a signal processing unit 120. The signal processing unit 120 may be operable to adjust the gain of the Doppler signal. The signal processing unit 120 may be further operable to perform first signal processing upon the Doppler signal for reducing noise in estimating a Doppler frequency by using continuity of a velocity of a blood flow. The signal processing unit 120 may be further operable to perform second signal processing upon the Doppler signal for compensating for aliasing of the Doppler signal. The Doppler frequency may represent a frequency shift between a frequency of the ultrasound signal transmitted to the target object and a frequency of the Doppler signal received at the probe.

Figure 2:
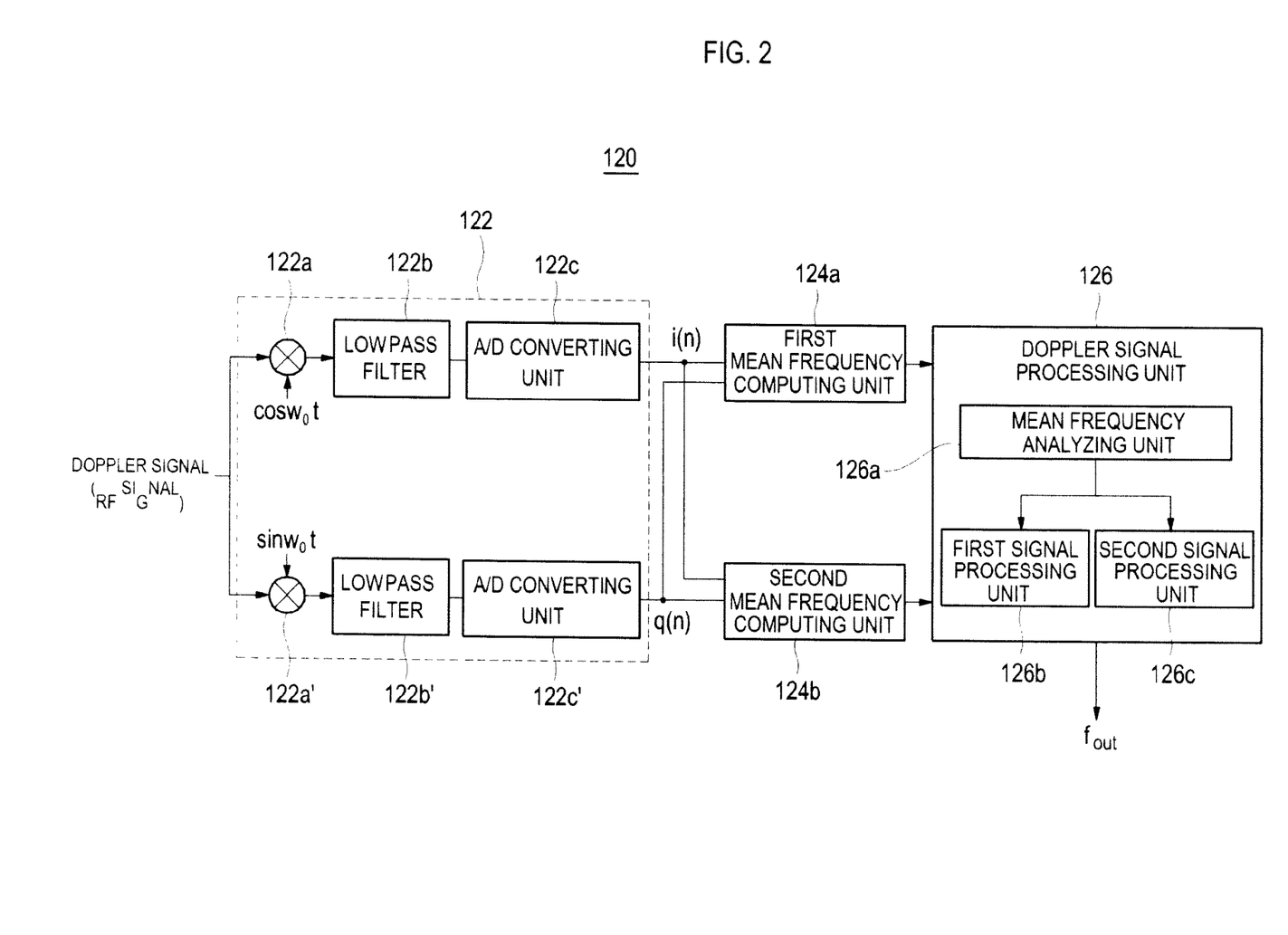
FIG. 2 is a block diagram showing one embodiment of a signal processing unit.

FIG. 2 is a block diagram showing one embodiment of the signal processing unit 120. As shown in FIG. 2, the signal processing unit 120 may include a quadrature demodulating unit 122. The quadrature demodulating unit 122 may be configured to demodulate the Doppler signal into a baseband signal including an I signal i(n) of an in-phase component and a Q signal q(n) of a quadrature component. The quadrature demodulating unit 122 may include multipliers 122a and 122a', lowpass filters 122b and 122b' and analog-to-digital converters (ADCs) 122c and 122c'. The multipliers 122a and 122a' may multiply the Doppler signals inputted from the transmission/reception unit 110 by a cosine function $\cos \omega_0 t$ and a sine function $\sin \omega_0 t$, respectively. The lowpass filters 122b and 122b' may perform lowpass filtering upon signals outputted from the multipliers 122a and 122a'. The ADCs 122c and 122c' may convert signals outputted from the lowpass filters 122b and 122b' into digital signals.

The signal processing unit 120 may further include first and second mean frequency computing units 124a and 124b. The first mean frequency computing unit 124a may receive $n^{th}$ IQ signals and $(n-1)^{th}$ IQ signals and compute a first mean frequency of the Doppler signal based on the $n^{th}$ and $(n-1)^{th}$ IQ signals. In one embodiment, the first mean frequency computing unit 124a may compute the first mean frequency through autocorrelation as in the following equation:

$$\text{First mean frequency} = \frac{PRF}{2\pi} \tan^{-1} \frac{\sum_{n=1}^{N} i(n-1)q(n) - i(n)q(n-1)}{\sum_{n=1}^{N} i(n)i(n-1) + q(n)q(n-1)} \quad (1)$$

where i(n) represents an $n^{th}$ I signal outputted from the quadrature demodulating unit 122, q(n) represents an $n^{th}$ Q signal outputted from the quadrature demodulating unit 122, i(n−1) represents an $(n-1)^{th}$ I signal, q(n−1) represents an $(n-1)^{th}$ Q signal, and N represents an ensemble length.

The second frequency computing unit 124b may compute a second mean frequency of the Doppler signal based on $n^{th}$ IQ signals and $(n-k)^{th}$ IQ signals, wherein k is a positive integer equal to or greater than 2. In one embodiment, the second frequency computing unit 124b may compute the second frequency of the Doppler signal based on $n^{th}$ IQ signals and $(n-2)^{th}$ IQ signals. That is, the second mean frequency computing unit 124a may compute the second mean frequency through autocorrelation as in the following equation:

$$\text{Second mean frequency} = \frac{PRF}{4\pi} \tan^{-1} \frac{\sum_{n=1}^{N} i(n)q(n-2) - i(n-2)q(n)}{\sum_{n=1}^{N} i(n)i(n-2) + q(n)q(n-2)} \quad (2)$$

Figure 3:
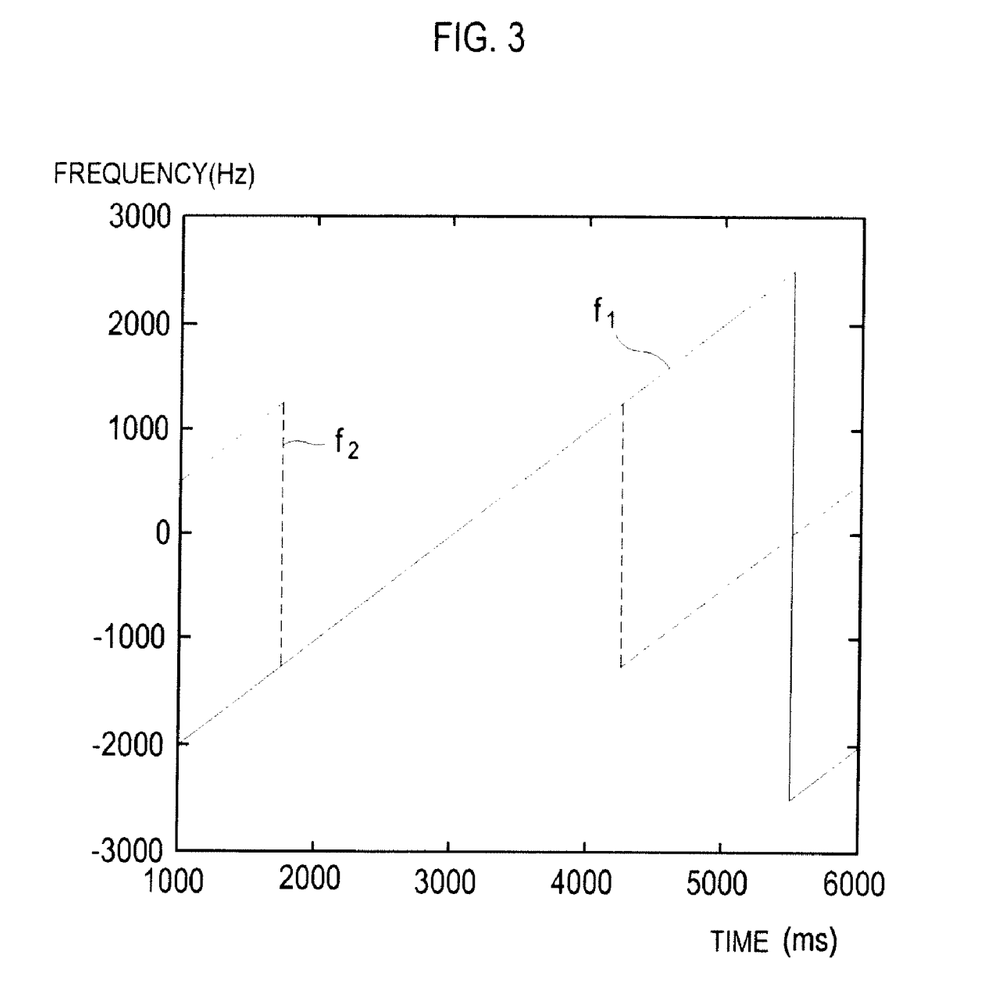
FIG. 3 is a graph showing first and second mean frequencies for an ideal Doppler signal in the absence of noise.
Figure 4:
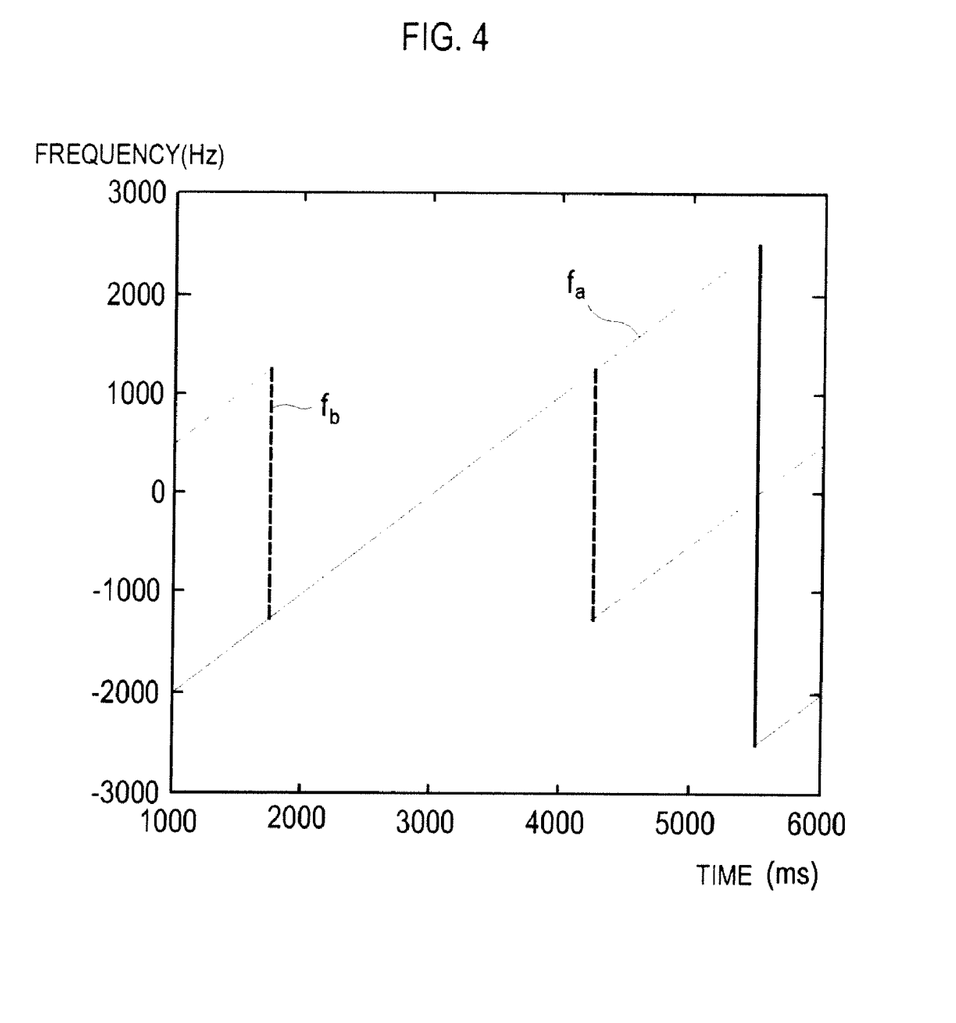
FIG. 4 is a graph showing first and second mean frequencies for a Doppler signal in the presence of noise.
Figure 5:
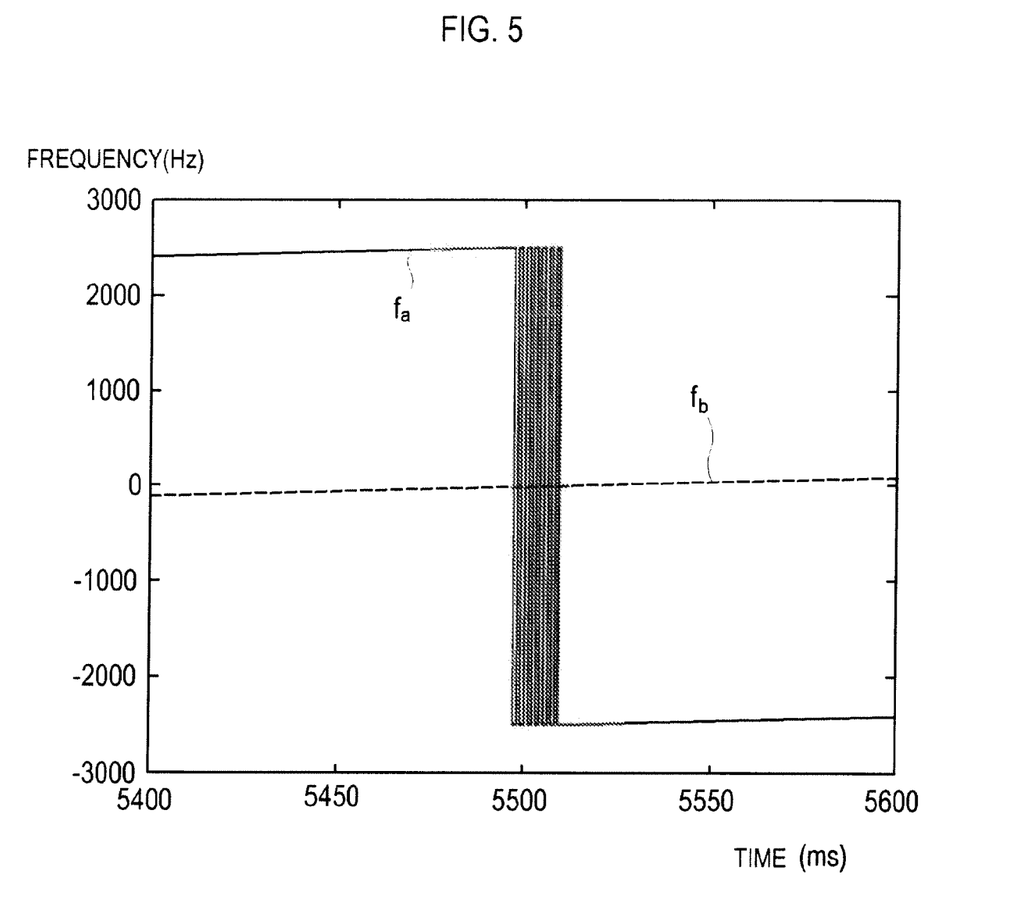
FIG. 5 is a graph showing first and second mean frequencies in a specific time interval (e.g., 5400 ms to 5600 ms) shown in FIG. 4.

Hereinafter, characteristics of the first and second mean frequencies outputted from the first and second mean frequency computing units 124a and 124b will be described by referring to FIGS. 3 and 5. FIG. 3 is a graph showing the first and second mean frequencies $f_1$ and $f_2$ for an ideal Doppler signal in the absence of noise. FIG. 4 is a graph showing the first and second mean frequencies $f_a$ and $f_b$ for a Doppler signal in the presence of noise. FIG. 5 is a graph showing the first and second mean frequencies $f_a$ and $f_b$ within a specific time interval (e.g., 5400 ms to 5600 ms) in FIG. 4. The first and second mean frequencies in FIGS. 3 and 4 may be computed by using equations (1) and (2).

Referring to FIG. 3, aliasing of the first mean frequency $f_1$ occurs once at about 5500 ms, and aliasing of the second mean frequency $f_2$ occurs once at each of about 1800 ms and 4200 ms. As shown in FIGS. 4 and 5, however, aliasing of the first mean frequency $f_a$ alternately occurs multiple times at about 5500 ms, and aliasing of the second mean frequency $F_b$ alternately occurs multiple times at each of about 1800 ms and 4200 ms. That is, the first mean frequency $f_a$ varies multiple times from +PRF/2 to −PRF/2 and/or from −PRF/2 to +PRF/2 at about 5500 ms, and the second mean frequency $f_b$ varies from +PRF/4 to −PRF/4 and/or from −PRF/4 to +PRF/4 at about 1800 ms and 4200 ms.

Referring back to FIG. 2, the signal processing unit 120 may further include a Doppler signal processing unit 126. The Doppler signal processing unit 126 may be operable to perform the first signal processing and the second signal processing based on the first and second mean frequencies. The Doppler signal processing unit 126 may include a mean frequency analyzing unit 126a that may be operable to analyze the first and second mean frequencies outputted from the first and second mean frequency computing units 124a and 124b, respectively, thereby outputting analysis result signals.

The mean frequency analyzing unit 126a may analyze the first and second mean frequencies to check whether aliasing occurs in the first and second mean frequencies. If the aliasing of the first and second mean frequencies does not occur, i.e., the Doppler frequency exists within a first frequency range (i.e., −PRF/4<Doppler frequency<PRF/4), the mean frequency analyzing unit 126a may output a first analysis result signal. If the aliasing of the first mean frequency does not occur in a negative frequency region and the aliasing of the second mean frequency occurs, i.e., the Doppler frequency exists within a second frequency range (i.e., −PRF/2<Doppler frequency <−PRF/4), the mean frequency analyzing unit 126a may output a second analysis result signal. If the aliasing of the first mean frequency does not occur in a positive frequency region and the aliasing of the second mean frequency occurs, i.e., the Doppler frequency exists within a third frequency range (i.e., PRF/4<Doppler frequency<PRF/2), the mean frequency analyzing unit 126a may output a third analysis result signal.

Further, if the first mean frequency varies multiple times at the maximum frequencies (±PRF/2) and the second mean frequency increases, then the mean frequency analyzing unit 126a may output a fourth analysis result signal. If the first mean frequency varies multiple times at the maximum frequencies (±PRF/2) and the second mean frequency decreases, the mean frequency analyzing unit 126a may output a fifth analysis result signal.

The Doppler signal processing unit 126 may further include a first signal processing unit 126b and a second signal processing unit 126c. The first signal processing unit 126b may be operable to perform the first signal processing to reduce the noise in estimating the Doppler frequency based on the analysis result signals outputted from the mean frequency analyzing unit 126a. If the first analysis result signal is inputted from the mean frequency analyzing unit 126a, the first signal processing unit 126b may perform the first signal processing according to the following equation:

$$f_{out} = \frac{1^{st} \text{ mean frequency} + 2^{nd} \text{ mean frequency}}{2} \quad (3)$$

If the second analysis result signal is inputted from the mean frequency analyzing unit 126a, the first signal processing unit 126b may perform the first signal processing according to the following equation (4).

$$f_{out} = \frac{1^{st} \text{ mean frequency} + 2^{nd} \text{ mean frequency} - \frac{PRF}{2}}{2} \quad (4)$$

While the aliasing of the first mean frequency does not occur at the second frequency range, the aliasing of the second mean frequency occurs, as shown in FIG. 4. Therefore, the first signal processing unit 126b may compute a mean of the first and second frequencies using equation (4), so that the Doppler frequency may be accurately computed.

Also, if the third analysis result signal is inputted from the mean frequency analyzing unit 126a, the first signal processing unit 126b may perform the first signal processing using the following equation:

$$f_{out} = \frac{1^{st} \text{ mean frequency} + 2^{nd} \text{ mean frequency} + \frac{PRF}{2}}{2} \quad (5)$$

While the aliasing of the first mean frequency does not occur in the third frequency range, the aliasing of the second mean frequency occurs, as shown in FIG. 4. Therefore, the first signal processing unit 126b may compute a mean of the first and second frequencies such as the equation (5), so that the Doppler frequency may be accurately computed.

The second signal processing unit 126c may be operable to perform second signal processing to compensate for the aliasing of the Doppler signal based on the analysis result signal from the mean frequency analyzing unit 126a. In one embodiment, if the fourth analysis result signal is inputted from the mean frequency analyzing unit 126a, the second signal processing unit 126c may perform the second signal processing to compensate for the aliasing by adding PRF to the first mean frequency aliased in a −PRF/2 direction. If the fifth analysis result signal is inputted from the mean frequency analyzing unit 126a, the second signal processing unit 126c may perform the second signal processing to compensate for the aliasing by adding −PRF to the first mean frequency aliased in a PRF/2 direction.

The image processing unit 130 may be operable to form a Doppler mode image based on the Doppler signal outputted from the signal processing unit 120. The display unit 140 may display the Doppler mode image processed by the image processing unit 130.

Although it is described that the second mean frequency computing unit 124 computes the second mean frequency based on the $n^{th}$ IQ signals and the $(n-2)^{th}$ IQ signals outputted from the quadrature demodulating unit 122 in one embodiment, the computation of the second mean frequency is not limited thereto. The second mean frequency may be computed through the following equation (6) based on the $n^{th}$ IQ signals and $(n-k)^{th}$ IQ signals outputted from the quadrature demodulating unit 122, wherein k is an integer equal to or greater than 2. In such a case, the first, second and second frequency ranges may also accordingly vary.

$$\text{Second mean frequency} = \frac{PRF}{2k\pi}\tan^{-1}\frac{\sum_{n=1}^{N} i(n)q(n-k) - i(n-k)q(n)}{\sum_{n=1}^{N} i(n)i(n-k) + q(n)q(n-k)} \quad (6)$$

As mentioned above, the aliasing of the Doppler signal may be accurately detected, so that the aliasing may be compensated. Also, although the noise is contained in the Doppler signal, the effect of the noise may be reduced in estimating the Doppler frequency.

In accordance with one embodiment of the present invention, there is provided an ultrasound system, comprising: a transmission/reception unit operable to transmit/receive ultrasound signals in a pulse repetition frequency (PRF) to form an n number of Doppler signals; a signal processing unit operable to compute a first mean frequency based on an $n^{th}$ Doppler signal and an $(n-1)^{th}$ Doppler signal and a second mean frequency based on an $n^{th}$ Doppler signal and an $(n-k)^{th}$ Doppler signal, respectively, wherein k is a positive integer equal to or greater than 2, the signal processing unit being further operable to estimate a Doppler frequency and compensate for aliasing of the Doppler signals based on the first and second mean frequencies to thereby produce Doppler signals with the aliasing compensated; and an image processing unit operable to form a Doppler mode image based on the Doppler signals produced by the signal processing unit.

In accordance with another aspect of the present invention, there is provided a method of forming a Doppler mode image in an ultrasound system having a transmission/reception unit, a signal processing unit and an image processing unit, comprising: a) at the transmission/reception unit, transmitting/receiving ultrasound signals at a pulse repetition frequency (PRF) to form Doppler signals; b) at the signal processing unit, computing a first mean frequency based on an $n^{th}$ Doppler signal and an $(n-1)^{th}$ Doppler signal and a second mean frequency based on an $n^{th}$ Doppler signal and an $(n-k)^{th}$ Doppler signal outputted from the transmission/reception unit, respectively, wherein k is a positive integer equal to or greater than 2; c) at the signal processing unit, performing first and second signal processing for reducing noise in estimating a Doppler frequency and compensating for aliasing of the Doppler signal based on the first and second mean frequencies; and d) at the image processing unit, forming a Doppler mode image based on the Doppler signals outputted from the signal processing unit.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:

a transmission/reception unit operable to transmit/receive ultrasound signals in a pulse repetition frequency (PRF) to form an n number of Doppler signals;

a signal processing unit operable to compute a first mean frequency based on an $n^{th}$ Doppler signal and an $(n-1)^{th}$ Doppler signal and a second mean frequency based on an $n^{th}$ Doppler signal and an $(n-k)^{th}$ Doppler signal, respectively, wherein k is a positive integer equal to or greater than 2, the signal processing unit being further operable to check whether the first and second mean frequencies exist within predetermined frequency ranges associated with the PRF, respectively, to determine occurrence of aliasing in the Doppler signals and compensate for the aliasing of the Doppler signals to thereby produce Doppler signals with the aliasing compensated;

wherein the signal processing unit includes a quadrature demodulating unit operable to demodulate the Doppler signals into baseband signals consisting of an I signal of an in-phase component and a Q signal of a quadrature component, and wherein the signal processing unit is operable to compute the first and mean frequencies through following equations, $$\text{First mean frequency} = \frac{PRF}{2\pi}\tan^{-1}\frac{\sum_{n=1}^{N} i(n-1)q(n) - i(n)q(n-1)}{\sum_{n=1}^{N} i(n)i(n-1) + q(n)q(n-1)}, \text{ and}$$

-continued $$\text{Second mean frequency} = \frac{PRF}{2k\pi}\tan^{-1}\frac{\sum_{n=1}^{N}i(n)q(n-k)-i(n-k)q(n)}{\sum_{n=1}^{N}i(n)i(n-k)+q(n)q(n-k)}$$

wherein i(n) represents and nth I signal outputted from the quantrature demodulating unit, q(n) represents an nth Q signal outputted from the quadrature demodulating unit, i(n−1) represents an (n−1)I signal, q(n−1) represents an (n−1)$^{th}$ Q signal, n represents an ensemble length, i(n−k) represents an (n−k)$^{th}$ I signal outputted from the quadrature demodulating unit, and q(n−k) represents an (n−k)$^{th}$ Q signal outputted from the quadrature demodulating unit;
and
an image processing unit operable to form a Doppler mode image based on the Doppler signals produced by the signal processing unit.

2. The ultrasound system of claim 1, wherein the signal processing unit includes:
a mean frequency computing unit operable to compute the first and second mean frequencies based on the baseband signals; and
a Doppler signal processing unit operable to perform the first and second signal processing based on the first and second mean frequencies.

3. The ultrasound system of claim 2, wherein the mean frequency computing unit include:
a first mean frequency computing unit operable to compute the first mean frequency based on an n$^{th}$ IQ signal and an (n−1)$^{th}$ IQ signal outputted from the quadrature demodulating unit; and
a second mean frequency computing unit operable to compute the second mean frequency based on n$^{th}$ IQ signals and (n−k)$^{th}$ IQ signals outputted from the quadrature demodulating unit, wherein k is an integer equal to or greater than 2.

4. The ultrasound system of claim 2, wherein the Doppler signal processing unit includes:
a mean frequency analyzing unit operable to analyze the first and second mean frequencies to output analysis result signals;
a first signal processing unit operable to perform a first signal processing upon the Doppler signals in response to the analysis result signals; and
a second signal processing unit operable to perform a second signal processing upon the Doppler signals in response to the analysis result signals.

5. The ultrasound system of claim 4, wherein the mean frequency analyzing unit is operable to:
if the aliasing does not occur in the first and second mean frequencies, output a first analysis result signal,
if the aliasing does not occur in the first mean frequency at a negative frequency region and the aliasing occurs in the second mean frequency, output a second analyzing result,
if the aliasing does not occur in the first mean frequency at a positive frequency region and the aliasing occurs in the second mean frequency, output a third analyzing result,
if the first mean frequency varies multiple times at ±PRF/2 and the second mean frequency increases, output a fourth analysis result signal, and
if the first mean frequency varies multiple times at ±PRF/2 and the second mean frequency decreases, output a fifth analysis result signal.

6. The ultrasound system of claim 5, wherein the first signal processing unit is operable to perform the first signal processing through the following equation in response to the first analysis result signal $$f_{out} = \frac{1^{st}\text{ mean frequency}+2^{nd}\text{ mean frequency}}{2}.$$

7. The ultrasound system of claim 5, wherein the first signal processing unit is operable to perform the first signal processing through the following equation in response to the second analysis result signal $$f_{out} = \frac{1^{st}\text{ mean frequency}+2^{nd}\text{ mean frequency}-\frac{PRF}{2}}{2}.$$

8. The ultrasound system of claim 5, wherein the first signal processing unit is operable to perform the first signal processing through the following equation in response to the third analysis result signal $$f_{out} = \frac{1^{st}\text{ mean frequency}+2^{nd}\text{ mean frequency}+\frac{PRF}{2}}{2}.$$

9. The ultrasound system of claim 5, wherein the second signal processing unit performs the second signal processing by adding PRF to the first mean frequency aliased in a −PRF/2 direction in response to the fourth analysis result signal.

10. The ultrasound system of claim 5, wherein the second signal processing unit performs the second signal processing by adding −PRF to the first mean frequency aliased in a PRF/2 direction in response to the fifth analysis result signal.

11. A method of forming a Doppler mode image in an ultrasound system having a transmission/reception unit, a signal processing unit and an image processing unit, comprising:
a) at the transmission/reception unit, transmitting/receiving ultrasound signals in a pulse repetition frequency (PRF) to form an n number of Doppler signals;
b) at the signal processing unit, demodulating the Doppler signals into baseband signals consisting of I signal of an in-phase component and a Q signal of a quadrature component, and computing a first mean frequency based on an n$^{th}$ Doppler signal and an (n−1)$^{th}$ Doppler signal and a second mean frequency based on an n$^{th}$ Doppler signal and an (n−k)$^{th}$ Doppler signal outputted from the transmission/reception unit, respectively, wherein k is a positive integer equal to or greater than 2, wherein the first and mean frequencies are calculated through the following equations, $$\text{First mean frequency} = \frac{PRF}{2\pi}\tan^{-1}\frac{\sum_{n=1}^{N}i(n-1)q(n)-i(n)q(n-1)}{\sum_{n=1}^{N}i(n)i(n-1)+q(n)q(n-1)}$$

-continued $$\text{Second mean frequency} = \frac{PRF}{2\pi}\tan^{-1}\frac{\sum_{n=1}^{N} i(n)q(n-k) - i(n-k)q(n)}{\sum_{n=1}^{N} i(n)i(n-k) + q(n)q(n-k)}$$

wherein $i(n)$ represents an $n^{th}$ I signal outputted from the quadrature demodulating unit, $q(n)$ represents an $n^{th}$ Q signal outputted from the quadrature demodulating unit, $i(n-1)$ represents an $(n-1)^{th}$ I signal, $q(n-1)$ represents an $(n-1)^{th}$ Q signal, N represents an ensemble length, $i(n-k)$ represents an $(n-k)^{th}$ I signal outputted from the quadratue demodulating unit, and $q(n-k)$ represents an $(n-k)^{th}$ Q signal outputted from the quadrature demodulating unit;

c) at the signal processing unit, checking whether the first and second mean frequencies exist within predetermined frequency ranges associated with the PRF, respectively, to determine occurrence of aliasing in the Doppler signals and compensating for the aliasing of the Doppler signals to produce Doppler signals with the aliasing compensated; and d) at the image processing unit, forming a Doppler mode image based on the Doppler signals produced by the signal processing unit.

12. The method of claim 11, wherein the step c) includes:
c1) analyzing the first and second mean frequencies to output analysis result signals; and
c2) performing first and second signal processing in response to the analysis result signals.

13. The method of claim 12, wherein the step c1) includes:
if the aliasing does not occur in the first and second mean frequencies, outputting a first analysis result signal;
if the aliasing does not occur in the first mean frequency at a negative frequency region and the aliasing occurs in the second mean frequency, outputting a second analyzing result;
if the aliasing does not occur in the first mean frequency at a positive frequency region and the aliasing occurs in the second mean frequency, outputting a third analyzing result;
if the first mean frequency varies multiple times at +PRF/2 and the second mean frequency increases, outputting a fourth analysis result signal; and
if the first mean frequency varies multiple times at ±PRF/2 and the second mean frequency decreases, outputting a fifth analysis result signal.

14. The method of claim 13, wherein the c2) includes performing the first signal processing through the following equation in response to the first analysis result signal.

$$f_{out} = \frac{1^{st} \text{ mean frequency} + 2^{nd} \text{ mean frequency}}{2}.$$

15. The method of claim 13, wherein the c2) includes performing the first signal processing through the following equation in response to the second analysis result signal $$f_{out} = \frac{1^{st} \text{ mean frequency} + 2^{nd} \text{ mean frequency} - \frac{PRF}{2}}{2}.$$

16. The method of claim 13, wherein the c2) includes performing the first signal processing through the following equation in response to the third analysis result signal.

$$f_{out} = \frac{1^{st} \text{ mean frequency} + 2^{nd} \text{ mean frequency} + \frac{PRF}{2}}{2}.$$

17. The method of claim 13, wherein the c2) includes performing the second signal processing by adding PRF to the first mean frequency aliased in a −PRF/2 direction in response to the fourth analysis result signal.

18. The method of claim 13, wherein the c2) includes performing the second signal processing by adding −PRF to the first mean frequency aliased in a PRF/2 direction in response to the fifth analysis result signal.

* * * * *